(12) United States Patent
Royds

(10) Patent No.: US 8,211,715 B1
(45) Date of Patent: Jul. 3, 2012

(54) CONSUMER FOOD TESTING DEVICE PROVIDING REMOTE MONITORING

(75) Inventor: Robert B. Royds, Plainsboro, NJ (US)

(73) Assignee: Harrogate Holdings, Ltd. Co., Hamilton (BM)

( * ) Notice: Subject to any disclaimer, the term of this patent is extended or adjusted under 35 U.S.C. 154(b) by 0 days.

(21) Appl. No.: 13/296,379

(22) Filed: Nov. 15, 2011

(51) Int. Cl.
*G01N 33/53* (2006.01)

(52) U.S. Cl. ........ 436/807; 436/518; 436/164; 436/175; 436/177; 422/68.1; 422/58; 422/61; 340/572.1

(58) Field of Classification Search .................. None
See application file for complete search history.

(56) References Cited

U.S. PATENT DOCUMENTS

| | | | |
|---|---|---|---|
| 4,020,046 A | 4/1977 | King et al. | |
| 4,822,174 A * | 4/1989 | Deibel ........................ | 366/279 |
| 4,933,092 A | 6/1990 | Aunet et al. | |
| 5,075,078 A | 12/1991 | Osikowicz et al. | |
| 5,096,837 A | 3/1992 | Fan et al. | |
| 5,218,208 A | 6/1993 | Augier et al. | |
| 5,229,073 A | 7/1993 | Luo et al. | |
| 5,275,785 A | 1/1994 | May et al. | |
| 5,354,692 A | 10/1994 | Yang et al. | |
| 5,452,716 A | 9/1995 | Clift | |
| 5,504,013 A | 4/1996 | Senior | |
| 5,602,040 A | 2/1997 | May et al. | |
| 5,622,871 A | 4/1997 | May et al. | |
| 5,656,503 A | 8/1997 | May et al. | |
| 5,695,946 A | 12/1997 | Benjamin et al. | |
| 6,046,057 A | 4/2000 | Nazareth et al. | |
| 6,180,335 B1 | 1/2001 | Wilkins et al. | |
| 6,268,209 B1 | 7/2001 | Pierson et al. | |
| 6,277,650 B1 | 8/2001 | Nazareth et al. | |
| 6,441,142 B1 | 8/2002 | Burks et al. | |
| 6,565,808 B2 | 5/2003 | Hudak et al. | |
| 6,616,893 B1 | 9/2003 | Pham | |
| 6,828,110 B2 | 12/2004 | Lee et al. | |
| 7,098,040 B2 | 8/2006 | Kaylor et al. | |
| 7,527,765 B2 | 5/2009 | Royds | |
| 7,776,266 B2 | 8/2010 | Royds | |
| 2004/0018575 A1 | 1/2004 | Rappin et al. | |
| 2004/0132091 A1 | 7/2004 | Ramsey et al. | |
| 2004/0132211 A1 | 7/2004 | Li | |
| 2004/0259226 A1 | 12/2004 | Robey et al. | |
| 2005/0106652 A1 | 5/2005 | Massey et al. | |
| 2006/0290496 A1 * | 12/2006 | Peeters ..................... | 340/572.1 |
| 2007/0047382 A1 | 3/2007 | McCurdy et al. | |
| 2007/0054414 A1 | 3/2007 | Burgess-Cssier et al. | |

FOREIGN PATENT DOCUMENTS

WO  WO 2005/006959 A2  1/2005

OTHER PUBLICATIONS

*E coli* Facts, Organic Trade Association, Web Page last Updated Jun. 8, 2011.*

* cited by examiner

*Primary Examiner* — Sally Sakelaris
(74) *Attorney, Agent, or Firm* — Watov & Kipnes, P.C.; Kenneth Watov

(57) ABSTRACT

A consumer food testing device for testing for the presence of harmful contaminants in a food sample, includes a system for producing a visual cue upon detection of a harmful chemical, biological, and/or ionizing radiation contaminant; and a processing system responsive to the detection of a harmful contaminant, for transmitting the global position of the consumer testing device, the identity of the harmful contaminant, and the time and date to a remote monitoring facility.

25 Claims, 8 Drawing Sheets

CONSUMER FOOD TESTING DEVICE PROVIDING REMOTE MONITORING

RELATED PATENT

The present invention is related to both U.S. Pat. Nos. 7,776,266, and 7,527,765, issued on Aug. 17, 2010, and May 5, 2009, respectively, each entitled "Consumer Food Testing Device," the teachings of which are incorporated herein to the extent they do not conflict herewith.

FIELD OF THE INVENTION

The present invention relates to safety testing of foodstuffs, and more particularly to a portable testing device for use by consumers to detect the presence of harmful contaminants in foodstuff to avoid consumption of contaminated food.

BACKGROUND OF THE INVENTION

Recent events in the world have given rise to concerns about unconventional terrorist attacks using biological, chemical, and/or radioactive weapons of mass destruction. These events have further heightened international awareness of the vulnerability of food and water supplies of nations to terrorist attacks. Certain biological, chemical and/or radioactive agents can be used in such attacks to dangerously contaminate food and water supplies. Such contamination may have widespread destructive effects on a large population resulting in large numbers of fatalities, serious acute long-term health effects such as fetal abnormalities, paralysis, blindness, physical disfigurement, and mental debilitation, and chronic illnesses such as cancer. The deliberate contamination of food and water is a real and current threat.

The U.S. Centers For Disease Control and Prevention (CDC) has identified several harmful contaminants that can be critical agents for possible terrorist attacks. Among the high-priority biological agents ("Category A" agents) are *Bacillus anthraces* (anthrax) and *Clostridium botulinum* (botulism), both of which are deadly pathogens and can be used to contaminate food and water.

The majority of harmful contaminants identified by CDC were classified as "Category B" agents because they are moderately easy to disseminate and cause moderate morbidity and low mortality. Some of the Category B agents include *Salmonella* spp. such as *Salmonella typhimurium* and *Salmonella enteritidis*, *Shigella* spp. such as *Shigella dysenteriae*, *Escherichia* spp. such as *E. coli* 0104:H4, *E. coli* 0157:H7 and *E. coli* non-O157:H7 STEC, *Campylobacter* spp. such as *Campylobacter jejuni*, *Listeria* spp. such as *Listeria monocytogenes*, and the like. Recently, the German government experienced great difficulty in both managing, and identifying the source of an *E. coli* 0104:H4 outbreak. *E. coli* can cause extensive damage to the kidneys and other organs.

The CDC further identified certain chemicals as possible agents for terrorist attack. Those include pesticides, dioxins, furans, polychlorinated biphenyl (PCBs), cyanides, heavy metals such as arsenic, lead and mercury, and other natural and synthetic persistent toxins including mycotoxin and marine toxin. The CDC has warned that terrorists may use various combinations of these agents, and/or implement attacks in more than one location simultaneously.

These agents are also known to pose significant threat in the event that they are inadvertently introduced into the food and water distribution chain due to unintentional contamination of food (e.g., through processing failures or handling errors) unreated to terrorism. Major outbreaks of food poisoning occur all too frequently, sometimes affecting hundreds of thousands of people.

Some examples of large-scale outbreaks caused by unintentional contamination include, among other incidences, an outbreak of *Salmonella enteritidis* infection linked to a contaminated ice cream pre-mix sickened an estimated 224,000 people in 41 states in the U.S in 1984, an outbreak of *Salmonella typhimurium* infection linked to post-pasteurization contamination of milk from a U.S. dairy plant sickened approximately 170,000 people in 1985; an outbreak of hepatitis A, which may be the largest food borne disease incident in history, caused by tainted clams affected nearly 300,000 people in China in 1991; and an outbreak of *Escherichia coli* 0157:H7 linked to tainted radish sprouts served in school lunches sickened about 8,000 children with some dead in Japan in 1996.

The World Health Organization (WHO) has estimated that about two million children worldwide die from food and water contaminated by pathogenic microbes every year. In developed countries, one out of every three has suffered from some form of a food poisoning every year. It is estimated that about 76 million illnesses, 325,000 hospitalizations, and 5,000 deaths occur annually due to food/water contamination in the U.S.

Food poisoning from contamination with pesticides, natural and synthetic toxins, marine toxins, mycotoxins, heavy metals, cyanide, and other acutely toxic chemicals also have been reported. In one deadly incident in 1981, a cooking oil product sold in Spain contaminated with a chemical agent that killed over 800 people and injured about 20,000. In 1985, nearly 1,400 people in the U.S. reported becoming ill alter eating watermelon grown in soil treated with the pesticide aldicarb. During 1971-72, more than 6,500 people were hospitalized with neurological symptoms and 459 died after eating bread made from mercury-contaminated wheat in Iraq. Additionally, in the 1960's, more than 200 people in Japan suffered from mercury poisoning after eating highly contaminated fish caught in polluted waters.

In today's global marketplace, the contamination of food in one country can have a significant effect on public health in other parts of the world. In 1989, approximately 25,000 people in 30 states in the U.S. were sickened by *Salmonella* chester in cantaloupes imported from Mexico. In 1996 and 1997, 2,500 people in 21 states in the U.S. and two Canadian provinces developed *Cyclospora* infections after eating tainted Guatemalan raspberries.

Another food contaminant is ionizing radiation which can cause damage to human cells. For example, in Russia as a result of the infamous Chemobyl nuclear accident, about 4,000 people were exposed to harmful radiation, such as iodine 131 (I-131), which later caused these people to develop thyroid cancer. Also, in March of 2011, due to at least partial meltdown of a nuclear plant in Fukushima, Japan, high levels of radioactive materials entered the food supply on a continuing basis as efforts were continued to control damaged nuclear reactors. Japan placed restrictions on many foods including spinach and milk, that were produced in provinces exposed to the radiation from the Fukushima Daiichi Nuclear Plant. Iodine 131 (I-131). Cesium 137 (Cs 137), and Cesium 134 (Cs 134) were detected in food. Spinach from one farm in Hitachi, a town 45 miles away from the nuclear power plant, contained 27 times the amount of I-131, and four times the amount of Cesium considered safe. Raw milk from a dairy farm in Rate, over 18 miles from the Nuclear Plant contained I-131 levels 17 times higher than considered safe. High levels of I-131 can be absorbed in one's body through the consumption of milk, and can accumulate in the thyroid gland, causing thyroid cancer, as previously mentioned. Also high levels of cesium can damage cells and cause humans to develop other kinds of cancer. It took considerable time and testing efforts by Japanese technicians to determine the locations of food irradiated by the radiation seeping from the nuclear plant, and to as a result determine the food that had to be quarantined to prevent health damage to consumers. Since iodine I-131 has a half life of about eight days, it typically is a very dominate food contamination in at least the first few weeks after a nuclear reactor accident. Radioactive iodine may fall on land where cows are grazing, creating a major problem with contamination of milk. Radionuclides from a nuclear reactor accident may also fall as an invisible dust on fresh vegetables, causing radiation damage to consumers.

Although iodine 131 has a relatively short half-life of eight days, as indicated, other radiation products will remain a problem, such as ground contamination by radioactive cesium. Cesium-137 and Cesium-134 are nuclides having a half-life of about two years, and are produced in nuclear reactors rather than via nuclear explosions. As a result, people are exposed both externally by gamma radiation from the ground, and internally after consuming contaminated food containing radioactive cesium, for example. Although milk is a critical food stuff that can be readily contaminated by aforesaid irradiation products, meat, fresh water fish, and cereals can also be significant sources of these dangerous radioactive products. As to radioactive cesium that falls directly on soil, or is washed into the soil from grass or other vegetation by rain, it may be taken up by plants via the roots in subsequent years depending upon the type of soil. However, external gamma radiation from the ground may persist for three to five years, or longer, for cesium, and also for strontium radioactive products.

Accordingly, there is a need for a food testing device designed to implement rapid real-time testing of foodstuffs prior to consumption. There is a further need for a food testing device that is compact, portable and simple to use with little or no training in laboratory techniques. There is a further need for a food testing device that is designed to prevent or minimize the incidence of illness, injury and death caused by deliberate or unintentional contamination of food and water. In addition, as shown by recent major food contamination occurrences in Germany, and Fukushima, Japan, there is a need for a rapidly acting consumer food testing device that provides for transmitting to a remote monitoring facility the detection of contaminated food by the testing device, the identity of the food contaminate itself, the identity of the food, the source of the food, and the geographic location of the reporting consumer food testing device.

SUMMARY OF THE INVENTION

The present invention relates generally to a consumer food testing device useful for implementing rapid, real-time testing of foodstuffs prior to consumption. The food testing device of the present invention is compact and portable, and intended for use by a consumer at any location including their home or in a restaurant, for example. The food testing device of the present invention is designed to analyze and detect in food potentially harmful contaminants including chemical agents, biological agents and radioactive agents, and alert the user prior to consumption. The food testing device can further be adapted to detect food specific allergens that may cause the consumer to exhibit effects of hypersensitivity or allergic reaction. Also, means are included in one embodiment of the food testing device for permitting the identification of the food contaminant, the identity of the food tested and its source or origin, the geographic location of the testing device, and a transmission system for transmitting all or at least a portion of the aforesaid to a remote monitoring facility.

The food testing device of the present invention is capable of analyzing small amounts of food samples, and can be implemented by consumers without extensive training in laboratory techniques. The food testing device is simple and cost effective to construct and implement, its compact size greatly enhances portability and discreet operation, while effectively acting to prevent a user from consuming contaminated food.

The food testing device of the present invention is designed to process a food sample into a form that can be tested by test assays. The test assays utilized are preferably in the form of a dipstick assay including chromatographic assays such as flow through and lateral flow assays, or other dipstick assays. Most preferably, the test assay is a lateral flow assay in the form of a dipstick. The use of lateral flow assays yields a relatively simple one-step analysis process that can easily be implemented by inexperienced users.

In general, a lateral flow assay typically includes an elongated rectangular component, often of paper, nitrocellulose or other porous inert material, upon which are printed stripes or layers of assay reagents having particular affinity for a target substance (i.e., harmful contaminant). The lateral flow assay includes a sample end, which is dipped into a sample, and the fluid is drawn along the strip by capillary action. As the sample passes the zones of assay reagents, chemical reactions occur which may result in a visual cue or color change, which can be in the form of one or more stripes, for example. The visual cues or color changes in one embodiment of the invention are detected by a colorimeter.

In one aspect of the present invention, a method for providing a consumer device for testing for the presence of harmful contaminants in a food sample, and transmitting unsafe findings to a remote monitoring facility comprising the steps of:

forming in a substrate a vessel comprising an interior receiving area having an open top, wherein said interior receiving area is adapted for receiving a disposable sample container to hold a food sample;

installing at least one harmful contaminant detector into said substrate proximate said vessel for producing an output signal indicative of the presence of a harmful contaminant in the food sample;

installing a global positioning sensor (GPS) into said substrate, for providing a signal indicative of the geographic location of said device;

installing a microprocessor into said substrate;

installing transmission means into said substrate, for transmitting data to a remote monitoring facility;

programming said microprocessor for responding to both said output signal from said at least one harmful contaminant detector, and said GPS signal, for operating said transmission means to transmit data to said remote monitoring facility to advise of the detection of a harmful contaminant in a food sample, and the geographic location of the food sample.

In a further aspect of the present invention, there is provided a food testing device for testing for the presence of harmful contaminants in a food sample, which comprises:

a vessel adapted for holding a liquified food sample;

a liquifier operatively associated with said vessel for converting an unliquified food sample into a liquified food sample; and at least one test assay dispensable from the device, the test assay comprising at least one assay reagent having an affinity for at least one harmful contaminant, and capable of both detecting the presence of the harmful contaminant in the liquified food sample, and producing a visual cue upon recognition of the harmful contaminant.

Preferably, the food testing device further comprises a radiation detector disposed proximately to the vessel for indicating the presence of ionizing radiation in the food sample at amounts exceeding normal background levels to detect the presence of a radioactive agent as the harmful contaminant.

In another aspect of the present invention, there is provided a method for testing for the presence of a harmful contaminant in a food sample, comprising the steps of:

liquifying the food sample to yield a liquified food sample; and implementing at least one test assay comprising an assay reagent having an affinity for at least one harmful contaminant and capable of both detecting and visually indicating the presence of the harmful contaminant in the liquified food sample.

BRIEF DESCRIPTION OF THE DRAWINGS

The following drawings, in which like items may have the same reference designations, are illustrative of embodiments of the present invention and are not intended to limit the invention as encompassed by the claims forming part of the application, wherein;

DETAILED DESCRIPTION OF THE INVENTION

Figure 1:
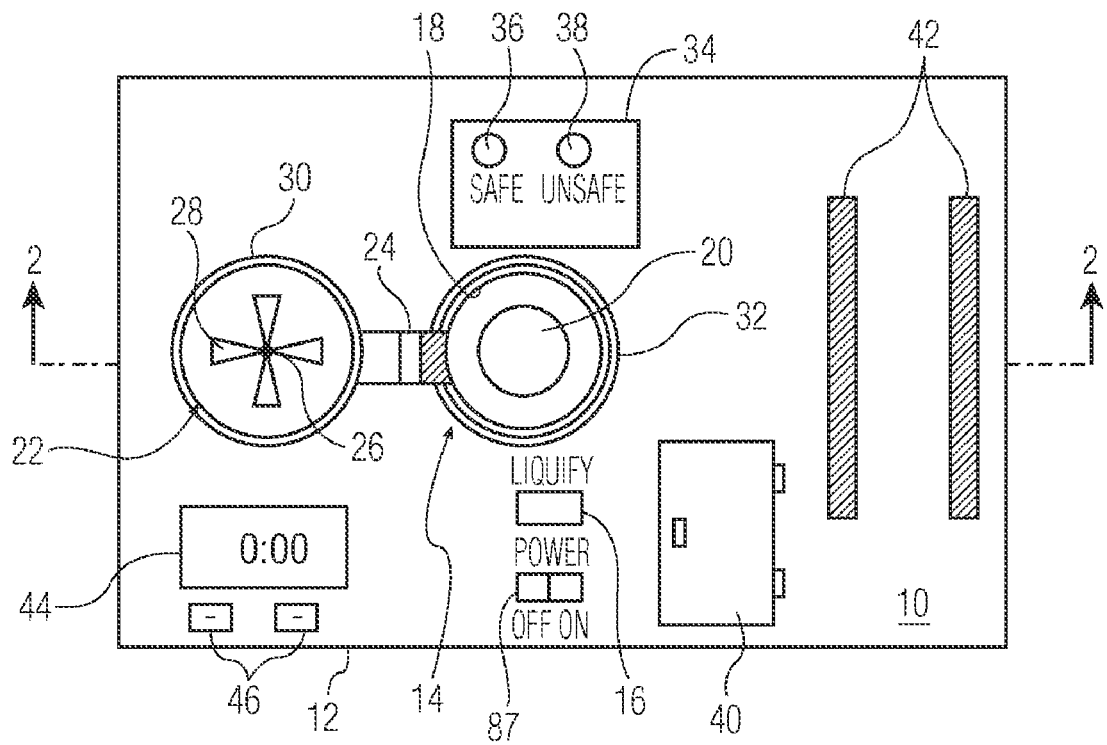
FIG. 1 is a top plan view of a food testing device for one embodiment of the present invention.

The present invention relates generally to a consumer food testing device useful for implementing rapid, real-time testing of foodstuffs prior to consumption, for preventing consumption of contaminated food. The food testing device of the present invention is intended for use by a consumer at any location including their home or in a restaurant. The food testing device of the present invention is designed to analyze and detect potentially harmful contaminants including chemical agents, biological agents and/or radioactive agents, and alert the user prior to consumption. The food testing device can be adapted to detect specific food allergens that may cause the consumer to exhibit effects of hypersensitivity or allergic reaction. The food testing device of the present invention is designed to analyze small amounts of food samples, and can be implemented by consumers without extensive training in laboratory techniques.

The food testing device of the present invention ensures that the food is safe for human consumption in a rapid, real-time manner, and is substantially free of harmful contaminants that can be dangerous to the consumer. The present invention operates to prevent or substantially minimize the incidence of food contamination due to improper handling or sabotage, while reducing the complexity of the testing process and the time needed to implement such tests. The food testing device is simple and cost effective to construct and implement, and its compact size greatly enhances portability and discreet operation.

In one embodiment of the present invention, there is provided a food testing device for testing the presence of harmful contaminants in a food sample, which comprises a vessel adapted for holding a liquified food sample; and at least one test assay dispensable from the device. The at least one test assay comprises at least one assay reagent having an affinity for at least one harmful contaminant, and capable of both detecting the presence of the harmful contaminant in the liquified food sample, and producing a visual cue upon recognition of the harmful contaminant.

In another embodiment of the present invention, the food testing device can further include a liquifier operatively associated with said vessel for converting an unliquified food sample into a liquified food sample.

Yet, In another embodiment of the present invention, the food testing device can further include a radiation detector disposed proximately to the vessel for indicating the presence of ionizing radiation in the food sample at amounts exceeding normal background levels to detect the presence of a radioactive agent as the harmful contaminant.

In combination with the above-mentioned embodiments, a preferred embodiment of the invention also includes a system and means for identifying the source or origin of the food, the date and time, the geographic position of the food testing device, and means for transmitting to a remote monitoring facility the aforesaid information, and data identifying the food contaminants detected as being unsafe.

Referring to FIG. 1, a food testing device is shown and identified generally by reference numeral 10. The food testing device 10 is preferably constructed to be small and compact for portability and discreet use, and is used to process and test small sample amounts of food and/or drinks for the presence of potentially harmful contaminants to provide enhanced consumption safety and prevent illnesses, injury and possibly death due to food poisoning.

Representative examples of potentially harmful contaminants include any of those selected from persistent toxic substances that can remain viable for long periods of time in food and water, and can readily be spread through food and drink products to the end consumer. Such persistent toxic substances can be chemical agents (e.g., heavy metals, pesticides, toxins, chemical substances), biological agents (e.g., pathogens, disease infections) or radioactive agents or combinations thereof, and/or specific allergens that may trigger adverse reactions in certain sizable portions of the population.

The food testing device 10 comprises a base or substrate 12 supporting a liquifier assembly 14 for converting food into a liquid or puree form. The liquifier assembly 14 includes a power switch 87 for electrical connection to a power source (not shown) such as a rechargeable battery, a vessel 18 for receiving and holding a disposable sample container 20, a blade assembly 22 of a liquifier 14 connected through a hinge 24 to the vessel 18, and a push button switch 16 for energizing the liquifier 14. The container 20 is adapted to receive and retain a small sample amount of food and/or liquid. The food testing device 10 can further include an optional container dispenser (not shown) located in the base 12 for dispensing a fresh disposable sample container 20 for each testing use.

The blade assembly 22 includes a blade housing 30 and a centrally-located spindle 26 extending from the blade housing 30 with a plurality of mixing blades 28 disposed therearound. The mixing blades 28 are configured to cut and break up any solids that may be present in the food sample and convert it into a puree form. The mixing blades 28 can be detached from the spindle 26 for cleaning. A motor (not shown) contained in the blade housing 30 mechanically drives the spindle 26 and the plurality of blades 28 during operation. Push button 16 is pushed to energize the liquifier motor (not shown).

The food testing device includes a radiation detector assembly 32 disposed around the vessel 18. The radiation detector assembly 32 is designed to detect and measure the presence of any ionizing radiation emanating from the food and/or liquid sample at amounts exceeding normal background radiation levels. The radiation detector assembly 32 informs the consumer of the amount of the ionizing radiation emanating from the food sample.

This information is conveyed through an indicator assembly 34 comprising a "safe" indicator light 36 and an "unsafe" indicator light 38. Alternatively, the indicator assembly can be a measurement gauge. If the level of the ionizing radiation is detected above a predetermined threshold for safety, the unsafe indicator 38 is activated to warn the consumer to avoid the respective food due to elevated levels of radioactivity, and possible contaminating presence of a radioactive agent. For example, generally caesium and strontium are found in milk, in which the safe levels of radioactivity should be below 1 kBq/Kg (one Kilobecquerel/Kilogram). Note that all other isotopes should have a radioactivity below 1 KBq/kg.

The radiation detection assembly 32 can be selected from any suitable ionization radiation detection devices including a Geiger counter, a scintillation counter, a photo multiplier, an ionization chamber, a semiconductor detector, a radiation dosimeter, and combinations thereof. For example, the radiation detection assembly can be utilized to detect the wavelengths for Iodine 131 (I-131), Cesium 134 (Cs-134) and/or Cesium (CS-137), but is not meant to be limited to detecting only the aforesaid radiation.

In an alternative embodiment, the radiation detection assembly can be in the form of a radioactive test assay utilizing chemical reagents to indicate the presence of a radioactive agent through reaction with the ionizing radiation emanating from the food sample. The radioactive test assay can be held proximate the food sample to detect dangerous ionizing radiation, in which the assay changes color or produces a visual cue as a visual indication of dangerous radioactivity contaminating the food sample.

The food testing device 10 further includes a test supply compartment 40 for accommodating and storing test assays (not shown) preferably in the form of dipstick assays including chromatographic assays such as flow through assays and lateral flow assays. Such test assays have been adapted for detecting specific components in a food sample through a simple one step process. A storage area 42 provides for holding the test assays during testing of the food sample as will be described hereinafter. The test assays are configured to receive a portion of the food sample from the liquifier assembly 14 after processing, to test the food sample for contaminants. A timer 44 with control buttons 46 allows the consumer to determine and monitor the completion of the test assays to check results.

The test assays are preferably in the form of a dipstick assay including chromatographic assays such as flow through assays or lateral flow assays, or other dipstick assays. Most preferably, the test assay is a lateral flow assay. Such test assays are known in the art, and can readily be constructed and designed by those skilled in the art to detect specific contaminants. They are also commercially available from various suppliers including, for example, the Food Safety segment of Neogen Corporation of Lansing, Mich. As discussed above the use of lateral flow assays yields a relatively simple one-step analysis process that can be implemented by inexperienced users. Suitable examples of commercial products include the REVEAL™ line of test assays marketed by Neogen Corp. for detecting *E. coli* O157:H7, *E. Coli* 0104: H4, *Listeria* spp., *Salmonella* spp., *Salmonella enteritidis*, peanut allergen, aflatoxin, deoxynivalenol and other dangerous substances in food and animal feed.

Generally, a lateral flow assay typically includes an elongated stick or rectangular component, often of paper, nitrocellulose or other porous inert material, upon which are printed stripes or layers of assay reagents having particular affinity for a target substance (i.e., harmful contaminant). The lateral flow assay includes a sample end, which is dipped into a sample, and the fluid is drawn along the strip by capillary action. As the sample passes the zones of assay reagents, chemical reactions occur which may result in visual cues or color changes, which can be in the form of one or more stripes, for example, to indicate the presence of one or more target substances or contaminants, in this example. Such lateral flow assays and assay reagents are known in the art.

A variety of reagents can be used to detect a range of analytes to alert the user of the presence of harmful contaminants and food allergens in foodstuffs, and can be derived from immunodiagnostic, enzymatic, lateral flow immunochromatography or chemistry type reactions. The reagent used in the test assays of the present invention can be any substance having a specific affinity for a target substance or analyte corresponding to food allergens or toxic substances, including chemical agents and biological agents that may be present in food stuffs and represent a dangerous threat to the health of the consumer.

Suitable reagents can be selected from those that can provide detection for harmful contaminants such as biological agents including, but not limited to, pathogens such as *Escherichia* spp. (e.g., *E. Coli* 0104:H4, and *E. coli* O157: H7), *Bacillus* spp. (e.g., *Bacillus anthracis* and *Bacillus cereus*), *Clostridium* spp. (e.g., *Clostridium botulinum* and *Clostridium perfringens*), *Campylobacter* spp. (e.g., *Campylobacter jejuni*), *Salmonella* spp. (*Salmonella enteritidis* and *Salmonella typhi*), *Listeria monocytogenes*, *Shigella* spp., *Streptococcus* spp., *Vibrio* spp. (e.g., *Vibrio cholerae*, *Vibrio parahemolyticus*, and *Vibrio vulnificus*), *Staphylococcus* spp (e.g., *Staphylococcus aureus*), *Yersinia* spp. (e.g, *Yersinia enterocolitica*), and the like, and chemical agents including, but not limited to, pesticides, toxins including ricin, botulin, aflatoxins, pyrrolizidine alkaloids, scombrotoxins, neurotoxin, mycotoxins such as ochratoxin A toxins, patulin toxins, *fusarium* toxins (e.g., fumonisins, trichothecenes including deoxynivalenol and zearelenone), and marine toxins such as ciguatera toxin, shellfish toxin, and tetrodotoxin, cyanide, nicotine, dioxin, polychlorinated phenyls, furans, heavy metals such as arsenic, lead, and mercury, histamine, histadine, and the like. The reagents can further be selected from those that can detect allergens such as those found in almonds, eggs, gliadin, milk, peanut, soy residues, and the like.

In a further embodiment of the present invention, suitable reagents can be selected from those that can provide detection for harmful contaminants such as radioactive agents including, but not limited to, radioactive isotopes of uranium, cesium, xenon, iodine, potassium, strontium, plutonium, iridium, and thorium.

Figure 2:
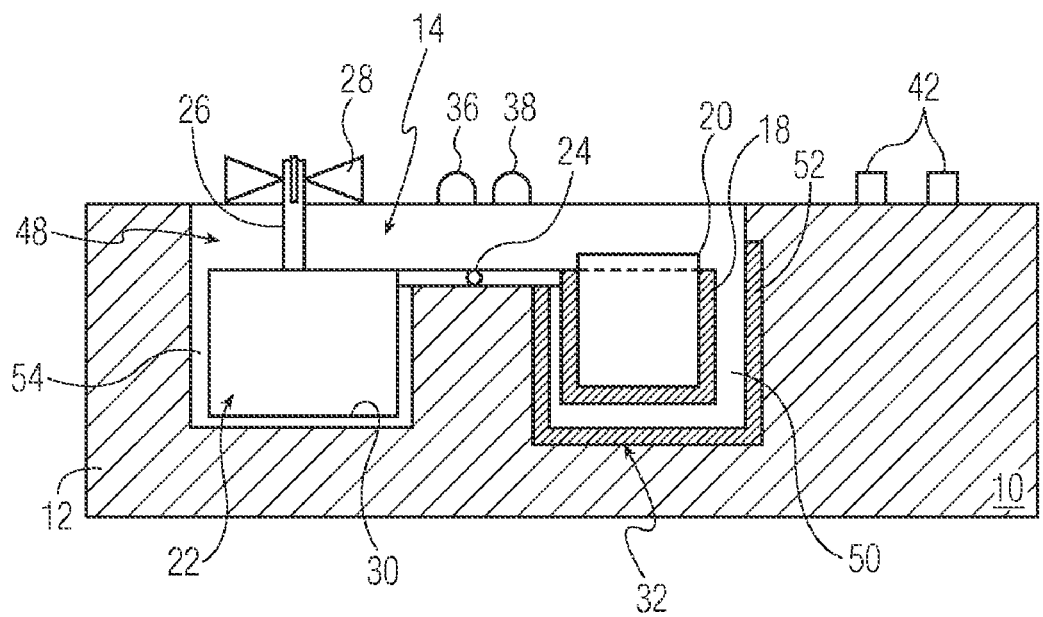
FIG. 2 is a partial cross-sectional view taken along lines 2-2 of FIG. 1 in accordance with the present invention.

Referring to FIG. 2, the food testing device 10 includes a recessed area 48 for accommodating the liquifier assembly 14. As discussed previously, the disposable container 20 holding the food sample, is retained in the vessel 18 of the liquifier assembly 14. The vessel 18 is located in a sample well 50 of the recessed area 48. The radiation detector assembly 32 includes an ionizing radiation sensor 52 extending along the sample well 50 around the vessel 18. The blade housing 30 of the blade assembly 22 is movable about the hinge 24 between open and closed positions. In the open position, the blade housing 30 occupies a holding well 54 of the recessed area 48. In the closed position, the blade housing 30 couples with the vessel 18 and encloses the disposable container 20. The mixing blades 28 draw into contact with the food sample held within the container 20. Note that a safety switch (not shown), only permits the energization of the liquifier motor (not shown) driving mixing blades 28 when in the closed position.

Once the housing 30 is securely coupled to the vessel 18, the blade assembly 22 is activated through the push button switch 16, provided power switch 47 is turned on. The mixing blades 28 are driven for a sufficient time to breakup the food sample and convert it into a soft paste or thick liquid form. During the blending of the food sample, the radiation detector assembly 32 can be used to measure the ionizing radiation in the food sample. The indicator assembly 34 (see FIG. 1) determines whether the measured ionizing radiation exceeds normal background radiation levels, and alerts accordingly. Indicator lights 36, 38 are individually turned on to indicate safe or unsafe radiation levels, respectively. Thereafter, the blade housing 30 is moved to an open position, and the mixing blades 28 are withdrawn from the container 20. A test assay can be implemented to analyze the food sample from the container as will be described hereinafter.

Figure 3:
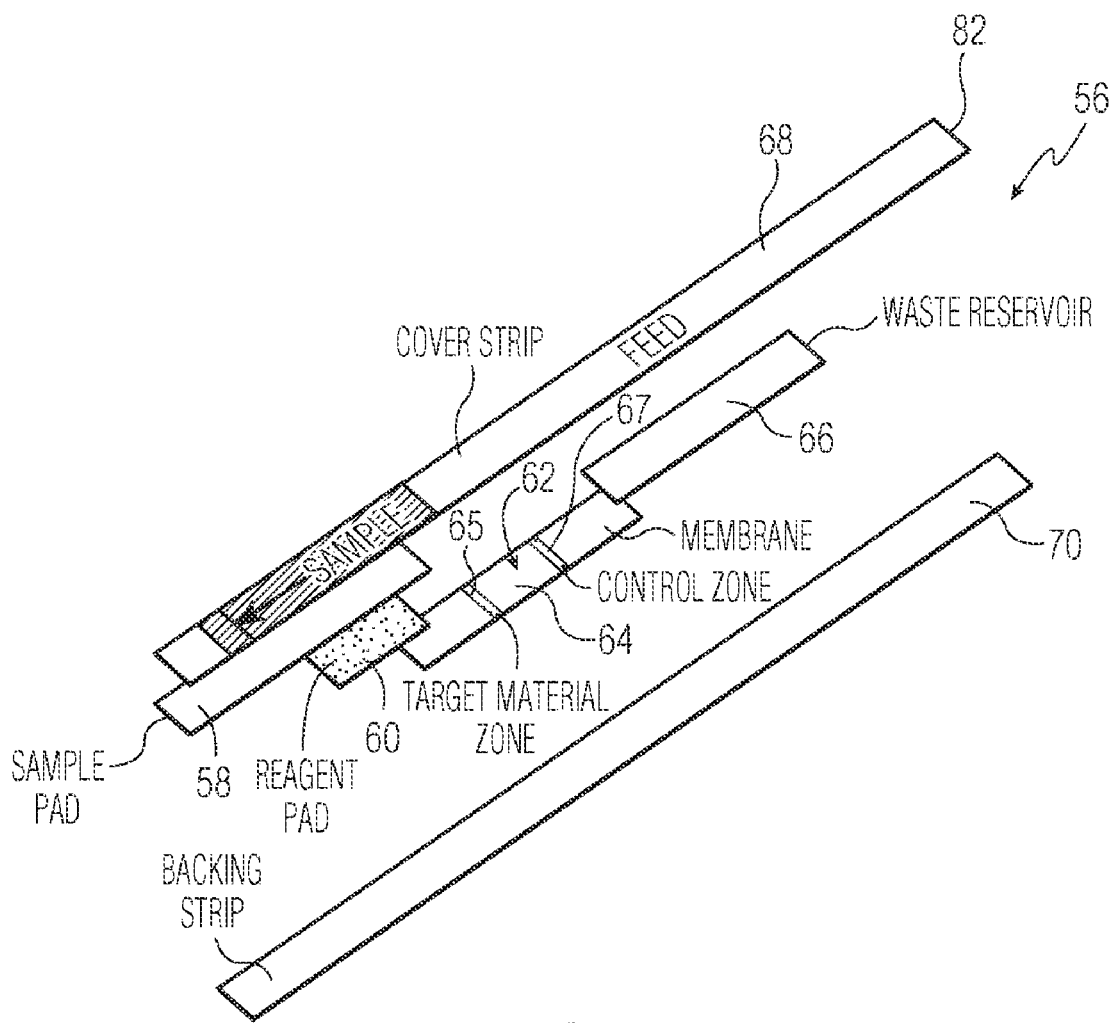
FIG. 3 is an exploded assembly view of a lateral flow assay for one embodiment of the present invention.

Referring to FIG. 3, a test assay is shown in the form of a lateral flow assay 56 for a preferred embodiment of the present invention. The lateral flow assay 56 is illustrated as an exploded assembly view. The lateral flow assay 56 can be fabricated to test for a single analyte or multiple analytes. The results of the assay 56 can be visually detected or machine-readable using suitable optical readers or scanners in combination with appropriate software programs. While the lateral flow assay 56 shown in FIG. 3 represents only one embodiment, it will be understood that the present invention is not limited as such.

As shown in FIG. 3, the lateral flow assay includes a sample pad 58 in contact with a reagent pad 60. The reagent pad 60 is in fluid communication with a membrane 62 comprising a test zone 64. The membrane 62 is in fluid communication with a waste reservoir 66. The sample pad 58, the reagent pad 60, the membrane 62 and the waste reservoir 66 are inserted and sandwiched between a cover strip 68 and a backing strip 70.

The sample pad 58 is disposed at the sample input end of the lateral flow assay 56. The sample pad 58 is dipped into the food sample, a portion of which is drawn through capillary action into the sample pad 58. The sample is then wicked from the sample pad 58 through the reagent pad 60, which contains reagents (e.g., antibodies) specific for a target substance or analyte representing the harmful food contaminant, conjugated to labeled or colored particles. If the target substance or contaminant is present, the target substance or contaminant binds to the particle conjugated reagent. The target substance-reagent-particle complex then leaves the reagent zone and travels through the membrane 62 into the test zone 64 thereof. The test zone 64 contains fixed anti-target substance reagents that captures the complex, and produce a visible cue such as a colored line 65. The remainder of the sample continues to migrate to the end of the membrane 62 where it is deposited into the waste reservoir 66.

The reagent pad 60 can further include a control immune complex that is eluted by the sample regardless of the presence of the target substance. The control conjugate migrates through the membrane 62 to the control zone where it forms a second visible cue such as a colored line 67. Regardless of the presence or absence of the target substance, the control line forms in the control zone to ensure the test assay is working properly. Note that a plurality of assays such as lateral flow assays 56 in the form of dipsticks can be held in the storage area 42, each for testing for a single contaminant. However, it is preferred that each test assay be capable of testing for a plurality of contaminants to the greatest extent possible.

Figure 4:
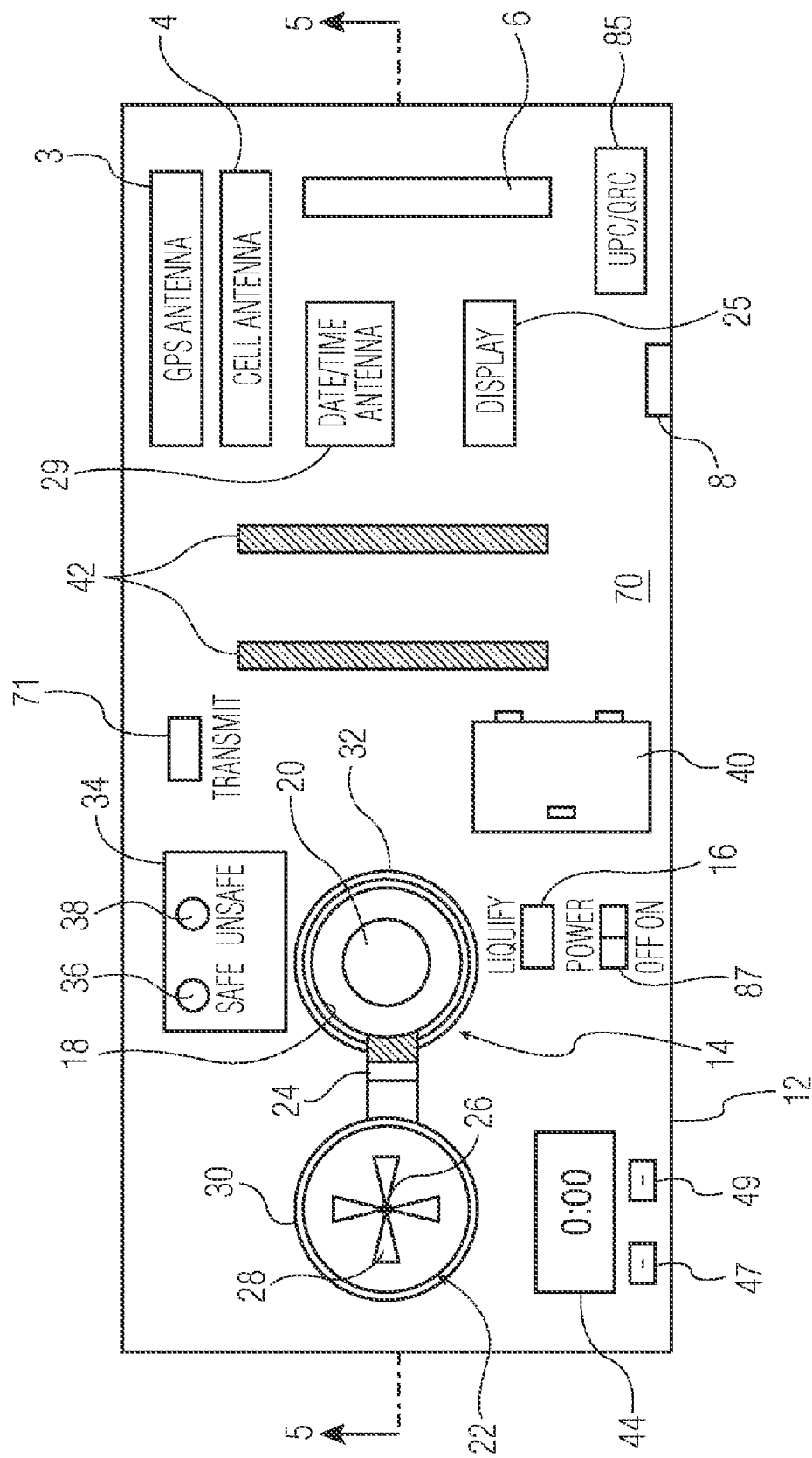
FIG. 4 is a top plan view of a food testing device for a second and preferred embodiment of the present invention.
Figure 5:
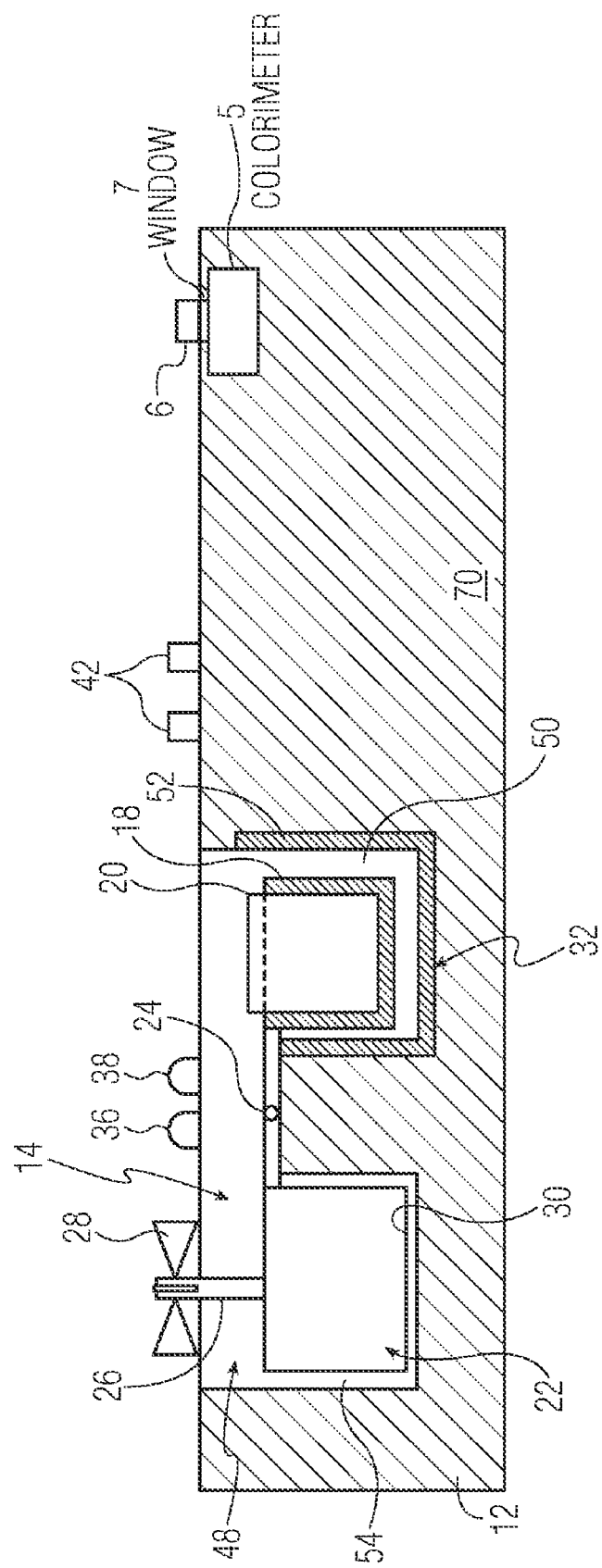
FIG. 5 is a partial cross-sectional view taken along lines 5-5 of FIG. 4 in accordance with the second embodiment of the invention.

FIGS. 4 through 9B show the preferred embodiment of the invention providing for transmitting from the improved consumer testing device 70, test results and other information as will be described below, to a remote monitoring facility 43. As shown in FIGS. 4 and 5, certain of the components for the first embodiment of the invention shown in FIGS. 1 through 3 have been retained, whereas other new components have been added, and certain other components modified. Specifically, control buttons 46 have been replaced by start radiation test button 47, and a start assay test button 49. Also, a transmit push button switch 71 has been added. A USB port 8 has been included to permit a computer, or other device to be connected to a microprocessor 27 (see FIG. 8) included in this preferred embodiment. Other newly added components as shown in FIGS. 4 and 5 include a GPS (Global Positioning Sensor) Antenna 3, a Cell Antenna 4, a Date/Time Antenna 29, test assay receiving slot 6, and a UPC/QRC scanning window 85.

Figure 6:
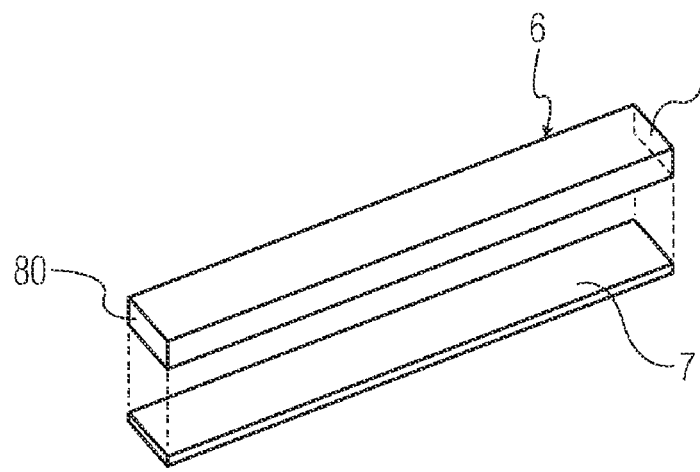
FIG. 6 is an exploded assembly view of a test assay receiving slot be positioned over the window for a colorimeter.
Figure 7:
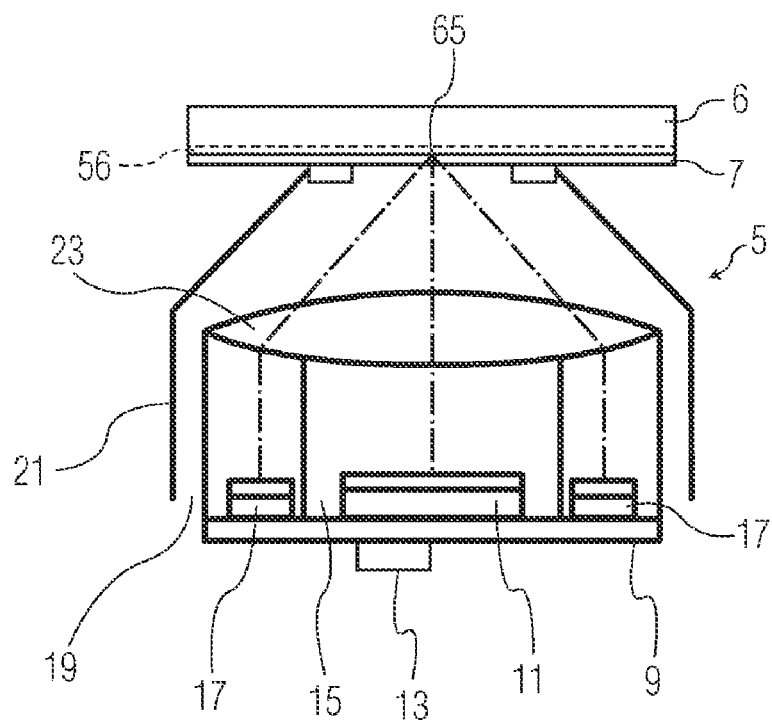
FIG. 7 is a simplified example of the design for a colorimeter for an embodiment of the invention.

In FIG. 6, an exploded assembly view is shown of the test assay receiving slot 6, and colorimeter window 7. As will be described in greater detail below the feed end of a test assay 56 is inserted into the open end 80 of the test assay receiving slot 6, and pushed into slot 6 until the end of the feed portion 82 of the test assay 56 strikes the closed end 9 of slot 6. An example of a compact colorimeter sensor 5 that can be installed into substrate 12 below the lest assay window 7 for detecting the color of the visual cue 65 resulting from a chemical or bacteriological food contaminant, for example. The colorimeter 5 includes a ceramic substrate 9, a photodetector 11, a temperature sensor 13, an inner band 15, a light emitting diode (LED) 17, an outer band 19, a sensor cone 21, and a lens 23 beneath the window 7. When a test assay 56 is pushed into test assay receiving slot 6, as previously described, the colorimeter 5 is operable to read the visual cue 65 resulting from a food contaminant test run. Specifically, the LED 17 is energized to project light through the lens 23 onto the visual cue 65 area of the test assay 56 strip. The photodetector 11 detects the color of light reflected back through the lens 23, provides a signal for processing by microprocessor 27 (see FIG. 8). In this example, two LEDs 17 are shown. Also, the temperature sensor 13 provides a signal to the microprocessor 27 indicative of the temperature at the time of running the assay test. Microprocessor 27 is programmed to determine from the temperature and wavelength of light received from the visual cue 65, whether the visual cue 65 color is representative of a chemical, bacteriological, or other food contaminant. If a food contaminant is identified, the microprocessor 27 is further programmed to store the results of the test in a memory 31, as will be further described below. Note that the colorimeter 5 is shown in FIG. 7 for purposes of providing an example of an appropriate visual cue 65 color sensor, but is not meant to be limiting.

Figure 8:
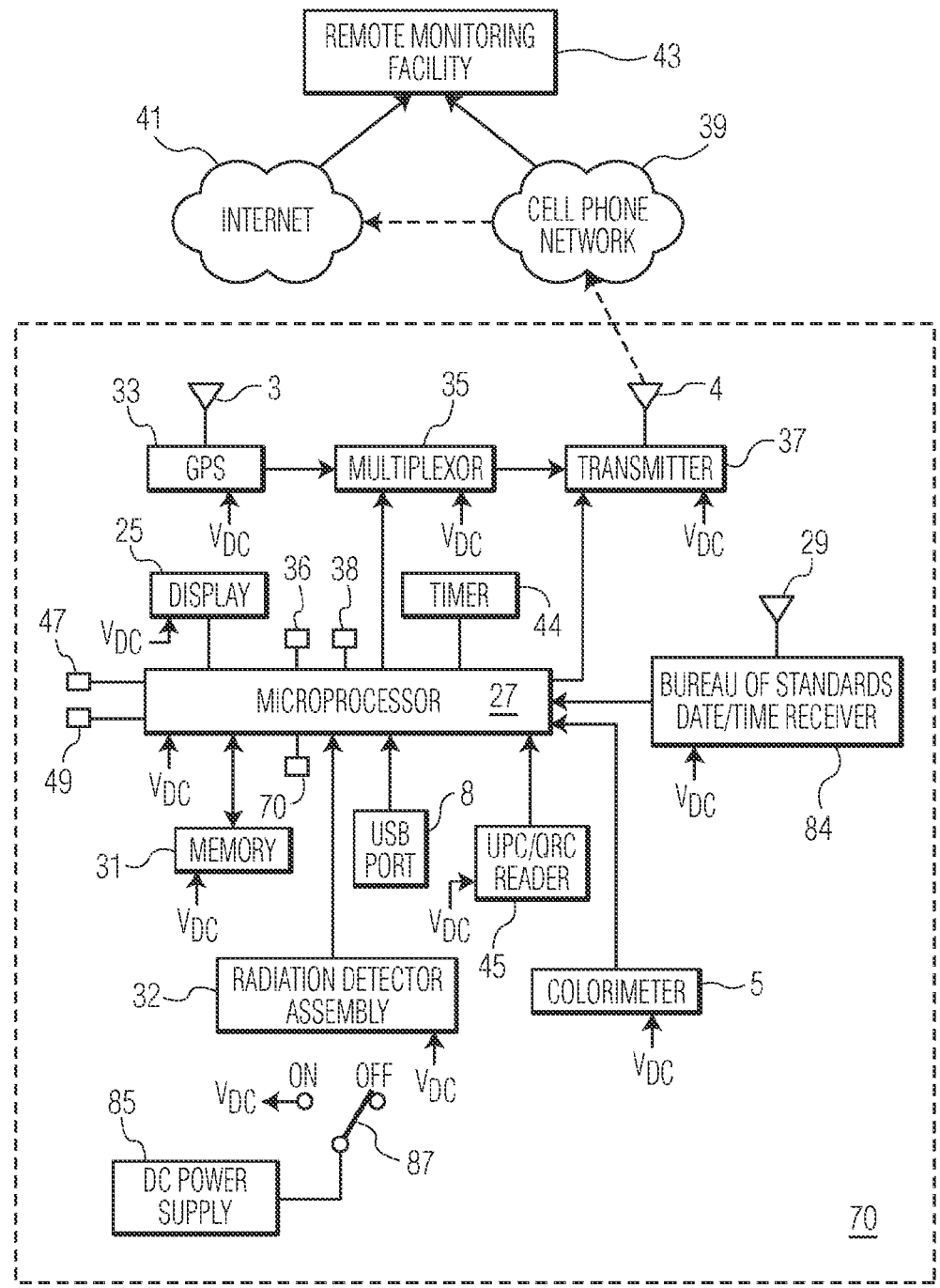
FIG. 8 is a block schematic diagram showing a system for providing the second embodiment of the invention.

FIG. 8 shows a block schematic diagram of various of the components included in the preferred embodiment food testing device 70. As shown, a DC power supply 85 provides power to various of the components via the power switch 87. A microprocessor 27 is programmed to respond to various test result signals, and other signals and data, for transmission to a remote monitoring facility 43, as will be described. A memory 31 is provided for microprocessor 27. USB port 8 is connected to the microprocessor 27. A radiation detector assembly 32 is connected to the microprocessor, as is a colorimeter 5, a UPC/QRC Reader 45, a start radiation test switch 47, a start assay test switch 49, a Bureau of Standards Date/Time Receiver 84, the Safe Indicator Light 36, the Unsafe Indicator Light 38, Display 25, a Tinier 44, and a Multiplexor 35. The GPS antenna 3 is connected to a GPS receiver 33, which in turn provides a geographic position signal to the Multiplexor 35. The output of the Multiplexor 35 is connected to a Transmitter 37, for transmitting multiplexed signals via antenna 4 through a cell phone network 39 either directly to a remote monitoring facility 43, or via the Internet 41 to a remote monitoring facility 43. Antenna 29 is connected to the Date/Time Receiver 84, for receiving the current date and time from the Bureau of Standards.

Figure 9A:
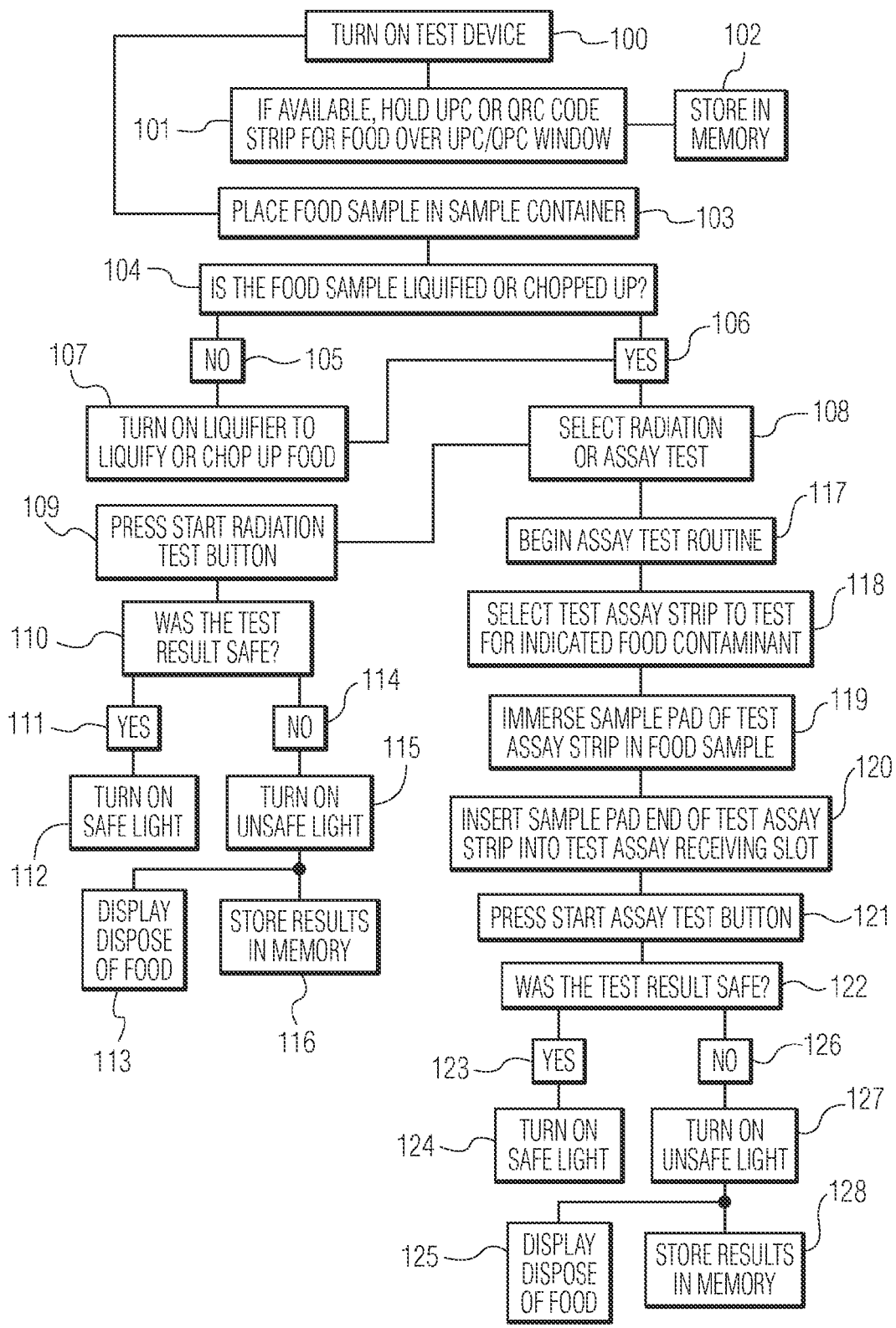
FIGS. 9A and 9B are flowcharts showing an example of the steps required for operating the consumer testing device for the second embodiment of the invention, including programming of an included microprocessor.
Figure 9B:
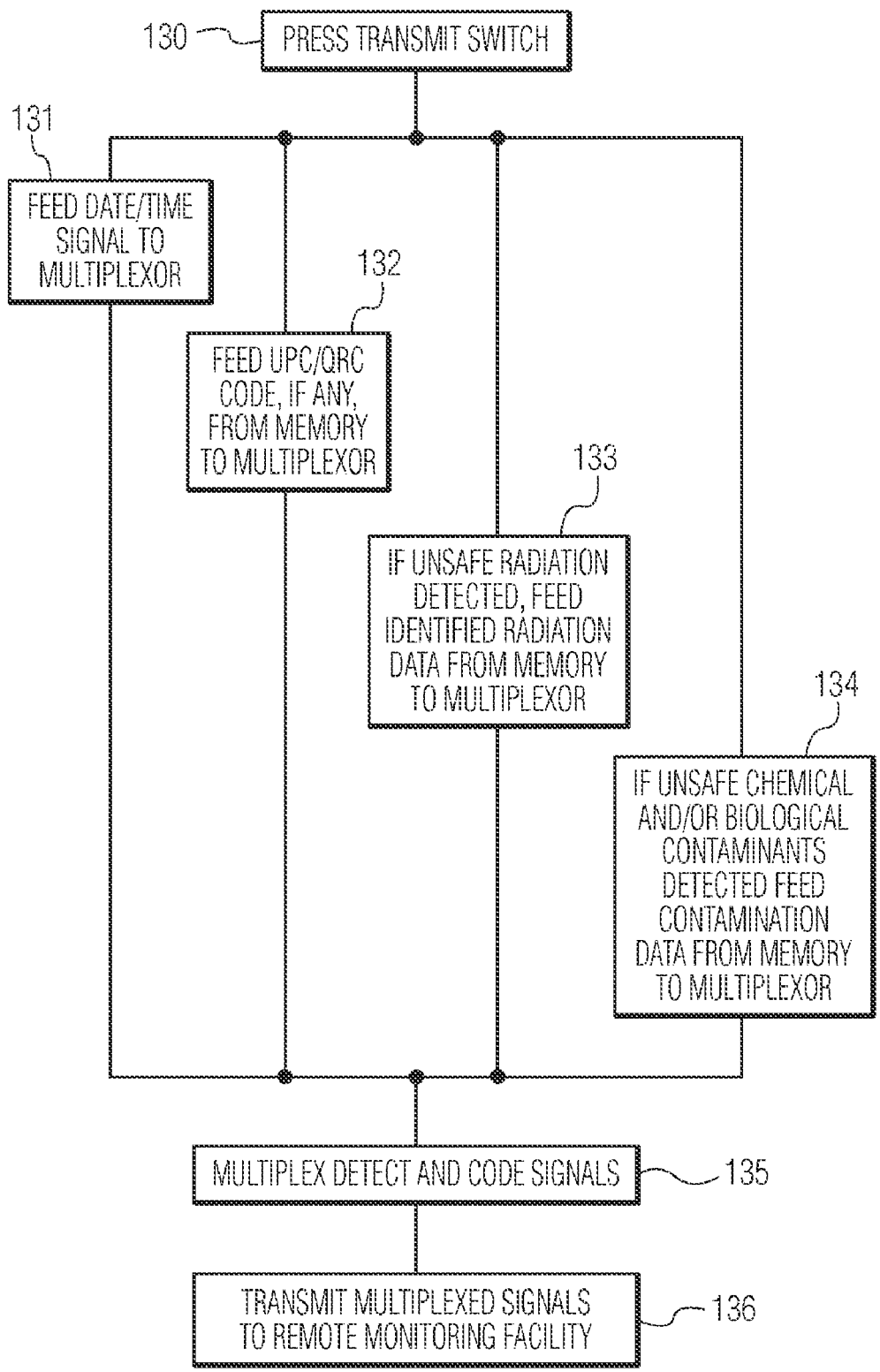

Microprocessor 27 is programmed to insure that steps 100 through 128 of FIG. 9A, and steps 130 through 136 of FIG. 9B are carried out as required. Reference is made to the flowcharts of FIGS. 9A and 9B for detailing the steps for operating the consumer food testing device 70 in a preferred embodiment of the invention.

The operation of the preferred embodiment for the consumer food testing device shown in FIGS. 4 through 9A and 9B will now be discussed. With reference to the flowchart of FIG. 9A, to initiate operation, a user first turns on the device 70 by operating the power switch 47, as shown in step 100. In Step 101, if the UPC or QRC code is available from the packaging for the food to be tested, the user places the code strip over the scanning window 85 of the UPC/QRC Reader 45. If such coding is detected and read, the UPC/QRC Reader 45 feeds the detected code signal for storage in the memory 31, as shown in step 102. However, if a UPC/CRC code strip is not available, a user would proceed directly to step 103 to place a food sample into the sample container 20. If the food sample is not liquified or chopped up as questioned in step 104, as verified in step 105, the user then proceeds to step 107 to turn on the liquifier assembly 14 by securing the blade housing 30 over the vessel 18, as previously described, followed by holding the liquifier push button switch 16 downward until the food sample is completely chopped up, or liquified. At that point, step 107 has been completed, whereafter the user proceeds to step 108, to determine whether they wish to run a radiation test or an assay test. If the user elects to run a radiation test, step 109 is entered by pressing the start radiation test button 47, causing microprocessor 27 to operate the radiation detector assembly 32 to test for radiation. If the test results show the food sample is free of a radiation contaminate, the microprocessor 27 turns on the "Safe" light 36, and no further action is taken. However, if the food sample is tested to contain unsafe radiation in step 114, the microprocessor 27 is programmed to turn on the "Unsafe" light 38 in step 115, and also to in step 113 display the wording "Dispose of Food," on display 25. Also, the microprocessor 27 will store the unsafe test result in step 116 into memory 31. If the user does not wish to run an assay test, they can elect to proceed to transmit switch 70, causing microprocessor 27 to transfer from memory 31 to multiplexor 35 the data showing that the food sample was found to be contaminated by unsafe radiation. Also, at this time, if a UPC/CRC code was obtained for showing the source and origin of the food sample, and identifying the food itself, microprocessor 27 will transfer from memory 31 the coded information to the multiplexor 35. Microprocessor 27 will also insure that Date/Time Signals from receiver 84, and GPS signals from the GPS receiver 33 are transferred to multiplexor 35. Multiplexor 35 operates to multiplex the aforesaid signals together and feed them to transmitter 37. Microprocessor 27 operates transmitter 37 to transmit via antenna 4 into a cell phone network 39 for direct transfer of the test results to a remote monitoring facility 43, or via the Internet 41 to the remote monitory facility 43.

As previously indicated, a user in step 108 selects whether to run a radiation test or an assay test. Assuming that a radiation test has been run as previously described, a user can also elect to run an assay test and vice versa. Obviously, the user could also have previously elected to not run a radiation test, and to only initiate an assay test routine as shown by step 117. The assay test routine begins in step 118 by the user selecting a test assay strip 56 that is indicative of testing for a particular food contaminant, whereby the food contaminant to be tested for is printed on the top of the cover strip 68 (such printing is not shown in FIG. 3). In step 119 the sample pad 58 of the assay strip 56 is immersed into the food sample after the blade housing 30 is removed from the sample container 20. In step 120, the user inserts the feed end of the test assay strip 56 with the food contaminant printing upright, via the sample pad 58 into the opening 80 of the test assay recovery slot 6, and pushes the test assay strip 56 there into until further inward movement is blocked by the closed end 9 of the recovery slot 6. Next, in step 121 the user presses the start assay test button 49, which action is responded to by microprocessor 27 for running the assay test by operating colorimeter 5 to obtain a signal indicative of the wavelength of the color shown by the visual cue 65, after a predetermined period of time from the beginning of the test. The microprocessor 27 will compare the wavelength of the color obtained with the wavelengths of corresponding food contaminants stored in memory 31 to determine if the food sample is safe and uncontaminated as shown in step 122. If yes as in step 123, microprocessor 27 turns on the "Safe" Light 36, as shown in step 124. If the food sample is contaminated (step 126), microprocessor 27 responds by turning on the "Unsafe" Light 38 (step 127), concurrently with step 125 to display on display screen 25 the message "Dispose of Food," and to store the results in memory 31, as shown in step 128. After receiving the unsafe test results, as previously indicated for obtaining an indication of unsafe radiation in the food, the user is instructed to depress the transmit switch 71, whereby the microprocessor 27 will respond by feeding the testing results from memory 31 to multiplexor 35, along with a GPS signal, Date/Time signal, UPC/QRC signal as previously indicated, for multiplexing and feeding to transmitter 37 from the output of multiplexor 35. Transmitter 37 is then operated by microprocessor 27, as previously indicated, to transmit via antenna 4 through a cell phone network 39, directly to a remote monitoring facility 43, or indirectly via the Internet 41 to the remote monitoring facility 43. Note that the flowchart of FIG. 9B for steps 130 through 136 shows the aforesaid steps for multiplexing and transmitting various of the aforesaid signal data to the remote monitoring facility 43. As shown in the flowchart of FIG. 9B, the information transmitted to remote monitoring facility 43 may only include "Unsafe" radiation test results, or only include "Unsafe" chemical and/or biological contaminant data, or in certain instances may include both radiation and test assay data results from steps 133 and 134, along with Date/Time data via step 131, and UPC/QRC coding via step 132 as shown.

The foregoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A method for providing a unitary reusable consumer device for testing for the presence of harmful contaminants in a food sample, and directly transmitting unsafe findings to a remote monitoring facility, comprising the steps of:
    forming in a substrate a vessel comprising an interior receiving area having an open top, said interior receiving area being adapted to hold a food sample;
    forming in said substrate a holding well within and opening from a top portion of said substrate;
    configuring said holding well to receive and store a food liquifier during inoperative states of said device;
    installing a hinge mechanism having one end secured to said liquefier, and another end secured into said substrate between said liquefier and said vessel, said hinge mechanism being adapted for rotating said liquefier from said holding well to said vessel, for positioning said blade assembly within said interior receiving area, for liquefying a food sample contained therein;
    installing at least one harmful contaminant detector into said substrate proximate said vessel for producing an output signal indicative of the presence of a harmful contaminant in the food sample;
    installing a global positioning sensor (GPS) into said substrate, for providing a signal indicative of the geographic location of said device;
    installing a microprocessor into said substrate;
    installing transmission means into said substrate, for directly transmitting data from said device to a remote monitoring facility; and
    programming said microprocessor for responding to both said output signal from said at least one harmful contaminant detector, and said GPS signal, for operating said transmission means to transmit data directly to said remote monitoring facility to advise of the detection of a harmful contaminant in a food sample, and the geographic location of the food sample.

2. The method of claim 1, wherein said at least one harmful contaminant detector is a radiation detector located proximate said vessel for detecting radiation emitted from food in said vessel, for indicating the presence or absence of harmful ionizing radiation in the food sample, wherein harmful radiation is indicated by amounts exceeding normal background levels of a radioactive agent.

3. The method of claim 1, wherein said installing steps for at least one harmful contaminant detector further includes the steps of:
    forming in said substrate a test assay supply compartment for containing at least one test assay, the test assay comprising at least one assay reagent having an affinity for at least one harmful contaminant; and
    forming in said substrate a visual means for reading a test assay activated by a food sample, for detecting a color change in a target zone of said test assay indicative of a particular harmful contaminant in said food sample, said visual means outputting a signal to said microprocessor indicative of the presence or absence of the harmful contaminant.

4. The method of claim 2, wherein said installing steps for at least one harmful contaminant detector further includes the steps of:
    forming in said substrate a test assay supply compartment for containing at least one test assay, the test assay comprising at least one assay reagent having an affinity for at least one harmful contaminant; and
    forming in said substrate a visual means for reading a test assay activated by a food sample, for detecting a color change in a target zone of said test assay indicative of a particular harmful contaminant in said food sample, said visual means outputting a signal to said microprocessor indicative of the presence or absence of the harmful contaminant.

5. The method of claim 1, wherein the step of installing said transmission means, further includes the steps of:
    installing a multiplexor in said substrate for multiplexing said GPS signal and an output signal from said microprocessor indicative of a detected harmful food contaminant, to provide a multiplexed output signal; and
    installing a transmitter in said substrate that is receptive of said multiplexed output signal, and responsive to a transmit signal from said microprocessor, for transmitting said multiplexed output signal to said remote monitoring facility.

6. The method of claim 5, wherein the step of transmitting is either directly via a cell phone network to said remote monitoring facility, or indirectly via said cell phone network through the Internet to said remote monitoring facility.

7. The method of claim 5, further including the step of:
    installing in said substrate a receiver for receiving signals indicative of the present date and time; and
    programming said microprocessor to be receptive date and time signals to provide a date/time signal to said multiplexor, for multiplexing with said GPS signal and said food contaminant signal, for transmission to said remote monitoring facility.

8. The method of claim 1, further including the steps of:
    installing first and second indicator lights on said substrate; and
    programming said microprocessor to turn on said first indicator light if a given food sample is tested safe, and to turn on said second indicator light if a given food sample is tested unsafe.

9. The method of claim 7, further including the steps of:
    installing a display on said substrate; and
    programming said microprocessor to normally display the date and time, and further to display upon completion of a test "Dispose Of Food" when a food sample is tested to be contaminated by unsafe bacteria, chemical, or radioactive agents.

10. The method of claim 2, further including the step of including a radiation detector capable of detecting at least I-131, Cs-137, and Cs-134, wherein upon detecting harmful radiation, said radiation detector further includes in its output signal an indication as to whether the radiation source is one of Iodine-131 (I-131), or Cesium 137 (Cs-137), or Cesium 134 (Ce-134).

11. The method of claim 3, wherein said at least one test assay is configured for detecting E. coli strain 0104:H4, and another is configured for detecting E. coli strain 0157:H7.

12. The method of claim 7, further including the steps of:
    installing a UPC/QRC reader in said substrate;

moving a UPC/QRC code label on a food package across a scan window of said UPC/QRC reader, which provides in response a data signal to said microprocessor, the data signal identifying the food in the food package, its origin, and date of packaging; and responsive to the signal from said reader, said microprocessor feeds an analogous data signal to said multiplexor for multiplexing with said GPS signal, said signal indicative of a harmful food contaminant, and said date/time signal, for transmission to said remote monitoring facility.

13. The method of claim 2, further comprising the step of selecting the radiation detector from the group consisting of a Geiger counter, a scintillation counter, a photo multiplier, an ionization chamber, a semiconductor detector, a radiation dosimeter and combinations thereof.

14. The method of claim 2, further including installing an indicator assembly on said substrate that is operatively associated with the radiation detector and microprocessor for informing the user of the presence of the radioactive agent.

15. The method of claim 3, further including the step of installing a timer in said substrate for tracking and measuring the time necessary to complete the detection process of the corresponding test assay.

16. The method of claim 3, wherein the test assay is a chromatographic assay.

17. The method of claim 16, further including the step of selecting the chromatographic assay from the group consisting of a dipstick assay, a flow through assay, a lateral flow assay, and combinations thereof.

18. The method of claim 3, wherein the assay reagent exhibits a particular affinity for a harmful contaminant selected from the group consisting of a biological agent, a chemical agent, a food allergen and combinations thereof.

19. The method of claim 18, wherein the biological agent is a pathogen.

20. The method of claim 19, further including the step of selecting the pathogen from the group consisting of *Escherichia* spp., *Bacillus* spp., *Clostridium* spp., *Campylobacter* spp., *Salmonella* spp., *Listeria monocytogenes, Shigella* spp., *Streptococcus* spp., *Vibrio* spp., *Staphylococcus spp, Yersinia* spp., and strains thereof, and combinations thereof.

21. The method of claim 20, further including the step of selecting the pathogen from the group consisting of *E. coli* 0104:H4, *E. coli* O157:H7, *Bacillus anthracis, Bacillus cereus, Clostridium botulinum, Clostridium perfringens, Campylobacter jejuni, Salmonella enteritidis, Salmonella typhi, Vibrio cholerae, Vibrio parahemolyticus, Vibrio vulnificus, Staphylococcus aureus, Yersinia enterocolitica* and combinations thereof.

22. The method of claim 18, further including the step of selecting the chemical agent from the group consisting of pesticides, toxins, ricin, botulin, aflatoxins, pyrrolizidine alkaloids, scombrotoxins, neurotoxin, mycotoxins, ochratoxin A toxins, patulin toxins, *fusarium* toxins, fumonisins, trichothecenes, deoxynivalenol and zearelenone, marine toxins, ciguatera toxin, shellfish toxin, and tetrodotoxin, cyanide, nicotine, dioxin, polychlorinated phenyls, furans, heavy metals, arsenic, lead, and mercury, histamine, histadine, and the combinations thereof.

23. The method of claim 18, further including the step of selecting the food allergen from the group consisting of almond, egg, gliadin, hazelnut, milk, peanut, soy residues and combinations thereof.

24. The method of claim 3, wherein said at least one test assay includes a plurality of assay reagents capable of detecting and producing visual cues for the presence of a plurality of harmful contaminants, respectively.

25. The method of claim 3, further comprising a plurality of test assays, each for detecting and producing a visual cue of a different harmful contaminant, respectfully, that may be present in the food sample.

* * * * *